United States Patent
Iida et al.

(10) Patent No.: US 10,405,422 B2
(45) Date of Patent: Sep. 3, 2019

(54) COPPER FILM-FORMING AGENT AND METHOD FOR FORMING COPPER FILM

(71) Applicant: SHIKOKU CHEMICALS CORPORATION, Kagawa (JP)

(72) Inventors: Shusaku Iida, Kagawa (JP); Takayuki Murai, Kagawa (JP); Hirohiko Hirao, Kagawa (JP)

(73) Assignee: SHIKOKU CHEMICALS CORPORATION, Marugame-shi, Kagawa (JP)

(*) Notice: Subject to any disclaimer, the term of this patent is extended or adjusted under 35 U.S.C. 154(b) by 0 days.

(21) Appl. No.: 14/413,532

(22) PCT Filed: May 30, 2013

(86) PCT No.: PCT/JP2013/065108
§ 371 (c)(1),
(2) Date: Jan. 8, 2015

(87) PCT Pub. No.: WO2014/010328
PCT Pub. Date: Jan. 16, 2014

(65) Prior Publication Data
US 2015/0189748 A1 Jul. 2, 2015

(30) Foreign Application Priority Data
Jul. 9, 2012 (JP) .................. 2012-154124

(51) Int. Cl.
| | | |
|---|---|---|
| *B05D 5/12* | (2006.01) | |
| *H05K 1/09* | (2006.01) | |
| *C23C 18/08* | (2006.01) | |
| *B05D 1/00* | (2006.01) | |
| *B05D 1/02* | (2006.01) | |
| *B05D 1/18* | (2006.01) | |
| *B05D 1/28* | (2006.01) | |
| *B05D 1/30* | (2006.01) | |
| *B05D 1/42* | (2006.01) | |
| *B05D 3/02* | (2006.01) | |
| *B05D 7/00* | (2006.01) | |
| *B05D 7/14* | (2006.01) | |
| *C07F 1/08* | (2006.01) | |
| *C22C 9/00* | (2006.01) | |
| *C23C 30/00* | (2006.01) | |
| *H05K 3/38* | (2006.01) | |

(52) U.S. Cl.
CPC .............. *H05K 1/09* (2013.01); *B05D 1/005* (2013.01); *B05D 1/02* (2013.01); *B05D 1/18* (2013.01); *B05D 1/28* (2013.01); *B05D 1/30* (2013.01); *B05D 1/305* (2013.01); *B05D 1/42* (2013.01); *B05D 3/0254* (2013.01); *B05D 7/00* (2013.01); *B05D 7/14* (2013.01); *C07F 1/08* (2013.01); *C22C 9/00* (2013.01); *C23C 18/08* (2013.01); *C23C 30/00* (2013.01); *C23C 30/005* (2013.01); *H05K 3/388* (2013.01); *Y10T 428/24917* (2015.01)

(58) Field of Classification Search
USPC ........................................................ 427/96.1
See application file for complete search history.

(56) References Cited

U.S. PATENT DOCUMENTS

| | | | |
|---|---|---|---|
| 4,818,255 | A | 4/1989 | Matsuura et al. |
| 5,106,462 | A | 4/1992 | Kawakami et al. |
| 5,496,590 | A * | 3/1996 | Maki .................. B23K 35/3615 427/388.1 |
| 6,831,009 | B2 | 12/2004 | Itabashi et al. |
| 6,989,329 | B2 | 1/2006 | Itabashi et al. |
| 7,510,639 | B2 | 3/2009 | Wang et al. |
| 7,662,981 | B2 | 2/2010 | Wang et al. |
| 8,268,157 | B2 | 9/2012 | Niazimbetova |
| 2002/0064947 | A1 | 5/2002 | Itabashi et al. |
| 2003/0124259 | A1 | 7/2003 | Kodas et al. |
| 2003/0148024 | A1* | 8/2003 | Kodas ..................... C23C 18/06 427/125 |
| 2003/0165623 | A1* | 9/2003 | Thompson .............. C07F 1/005 427/376.1 |
| 2004/0249063 | A1 | 12/2004 | Sterzel et al. |
| 2005/0003086 | A1 | 1/2005 | Otani et al. |
| 2005/0042366 | A1 | 2/2005 | Itabashi et al. |

(Continued)

FOREIGN PATENT DOCUMENTS

| | | |
|---|---|---|
| CN | 1357647 A | 7/2002 |
| CN | 1602314 A | 3/2005 |
| CN | 1733978 A | 2/2006 |
| CN | 101868563 A | 10/2010 |
| CN | 102276796 A | 12/2011 |
| EP | 0 368 231 A2 | 5/1990 |
| JP | 52-17335 A | 2/1977 |
| JP | 06-181387 A | 6/1994 |
| JP | 2005-2471 A | 1/2005 |
| JP | 2005-35984 A | 2/2005 |
| JP | 2005-513117 A | 5/2005 |
| JP | 2009-256218 A | 11/2009 |
| JP | 2012-112022 A | 6/2012 |
| KR | 10-2012-0064484 A | 6/2012 |
| WO | 03/053895 A2 | 7/2003 |

OTHER PUBLICATIONS

Communication dated Feb. 17, 2016 issued by European Patent Office in counterpart European Application No. 13816923.0.

(Continued)

*Primary Examiner* — Austin Murata
(74) *Attorney, Agent, or Firm* — Sughrue Mion, PLLC (57) ABSTRACT

The present invention is a copper film-forming agent containing a copper complex composed of a copper formate and a 5-membered or 6-membered nitrogen-containing heterocyclic compound having from 1 to 3 nitrogen atoms, in which the nitrogen-containing heterocyclic compound has one or two ring structures, the total number of carbon atoms contained in a substituent is from 1 to 5, and an element other than a carbon atom in the compound is not bonded to a hydrogen atom.

8 Claims, 2 Drawing Sheets

(56) References Cited

U.S. PATENT DOCUMENTS

| | | | |
|---|---|---|---|
| 2005/0173678 A1* | 8/2005 | Miura | C23F 11/10 252/394 |
| 2006/0016693 A1 | 1/2006 | Wang et al. | |
| 2006/0096867 A1* | 5/2006 | Bokisa | C25D 3/56 205/253 |
| 2006/0099343 A1* | 5/2006 | Thompson | C07F 1/005 427/250 |
| 2006/0204673 A1* | 9/2006 | Takayasu | C23C 16/401 427/585 |
| 2006/0210705 A1* | 9/2006 | Itoh | H01B 1/22 427/96.1 |
| 2008/0178761 A1 | 7/2008 | Tomotake et al. | |
| 2008/0223253 A1 | 9/2008 | Song et al. | |
| 2009/0139873 A1 | 6/2009 | Wang et al. | |
| 2010/0029969 A1 | 2/2010 | Otani et al. | |
| 2011/0056839 A1* | 3/2011 | Medina | C25D 5/08 205/176 |
| 2011/0220512 A1* | 9/2011 | Niazimbetova | C07D 233/60 205/297 |
| 2011/0220514 A1 | 9/2011 | Niazimbetova | |
| 2014/0097231 A1* | 4/2014 | Hirao | B23K 35/365 228/176 |

OTHER PUBLICATIONS

Extended European Search Report dated Jun. 7, 2016, by the European Patent Office in counterpart European Application No. 13816923.0.

Office Action dated May 18, 2016, by the Taiwanese Patent Office in counterpart Taiwanese Application No. 102119536.

Search Report dated Jul. 2, 2013 issued by the International Searching Authority in counterpart International Patent Application No. PCT/JP2013/065108 (PCT/ISA/210).

Written Opinion dated Jul. 2, 2013 issued by the International Searching Authority in counterpart International Patent Application No. PCT/JP2013/065108 (PCT/ISA/237).

M.A. Bernard et al.; "Etude de Quelques Composes du Formiate de Cuivre Solvate Par L'Imidazole et le Methyl-1-Imidazole"; Thermochimica Acta, vol. 98; 1986; pp. 139-145.

Communication dated Jan. 22, 2016, from the State Intellectual Property Office of People's Republic of China in counterpart Application No. 201380036469.4.

Office Action dated Nov. 30, 2016, issued by the State Intellectual Property of P.R. China in counterpart Chinese Application No. 201380036469.4.

Communication dated Apr. 6, 2017, issued by the European Patent Office in counterpart European application No. 13816923.0.

Communication dated Jul. 24, 2017 issued by the State Intellectual Property Office if the People's Republic of China in counterpart Chinese Patent Application No. 201380036469.4.

Office Action dated Aug. 16, 2016 issued by the Japanese Patent Office in counterpart Japanese Patent Application No. 2014-524689.

Communication dated Jul. 24, 2018, issued by the Indian Patent Office in counterpart Indian Application No. 149/DELNP/2015.

Communication dated Feb. 6, 2018, issued by the European Patent Office in counterpart European Patent Application No. 13816923.0.

Communication dated Feb. 7, 2018, issued by the State Intellectual Property Office of the People's Republic of China in counterpart Chinese Patent Application No. 201380036469.4.

Communication dated Jun. 20, 2018, from the European Patent Office in counterpart European Application No. 13816923.0.

Chinese Patent Office, Office Action (Notification of Reexamination) dated Jun. 24, 2019 in Chinese Patent Application No. 201380036469.4.

Korean Patent Office, Office Action (Notice to Submit Response) dated May 31, 2019 in Korean Patent Application No. 10-2015-7000590.

* cited by examiner

[FIG. 1]

| | 3,000 times | 30,000 times |
|---|---|---|
| Ex. 1 |  |  |
| Ex. 2 |  |  |
| Ex. 3 |  |  |
| Ex. 4 |  |  |
| Comp. Ex. 3 |  |  |
| Comp. Ex. 4 |  |  |

[FIG. 2]

COPPER FILM-FORMING AGENT AND METHOD FOR FORMING COPPER FILM

TECHNICAL FIELD

The present invention relates to a copper film-forming agent and a method for forming a copper film.

BACKGROUND ART

Copper is widely used as a wiring material because of its high electrical conductivity next to silver among all metals and inexpensiveness. For example, a technique of forming a circuit by forming a copper layer on a substrate and removing an unnecessary copper portion by means of etching has been classically used.

However, according to this method, because not only of a large number of treatment steps but also of a necessity of a treatment of an etching waste liquid, there was involved such a problem of a lot of costs and large in the load on the environment.

Meanwhile, put into practical use is a technique of forming a circuit by kneading copper particles and a resin binder with a solvent or the like to process into a paste and printing this, followed by heating and burning, whereby the resin binder is cured to keep contact of the copper particles with each other. However, according to this method, since a relatively large amount of the resin binder remains within a conductor even after forming a circuit, it was difficult to achieve sufficient electrical conductivity.

In addition, there is a known phenomenon in which by making metallic particles small in a nano-level size, the metallic particles are joined with each other by heating at relatively low temperature as if they melt together. Thus, developed is a technique in which copper particles are joined with each other by printing and heating and burning by utilizing this phenomenon, to form a circuit, thereby reducing a resin binder remaining within a conductor after the circuit formation. However, according to this method, since the copper particles must be processed into a nano-level size, there was involved such a problem that the manufacturing costs become high.

Meanwhile, a method for forming a circuit by printing a wiring pattern by using a copper composition capable of depositing copper by heat decomposition, followed by heating to deposit copper is proposed. According to this method, since it is not necessary to process the copper particles into a nano-level size, the manufacturing costs can be reduced. In addition, since a resin binder remaining within a conductor after forming a circuit can be reduced, good electrical conductivity can be achieved.

However, in a copper film formed by using such a technique, since only a small amount of or substantially no resin binder which contributes to adhesion to a base material is contained, the adhesion to the base material is ensured exclusively by a direct interaction between copper and the base material surface. Since copper is originally hydrophilic and the adhesion on the hydrophobic surface is not ensured, it is desirable that the base material surface is hydrophilic. For that reason, a composition that is aimed at being used in this application is required to have excellent affinity with the hydrophilic surface.

In addition, in order to reduce a heat load to the base material and to reduce the energy consumption, it is required that copper can be deposited at a lower temperature, specifically, copper can be deposited at a temperature of 130° C. or lower at which it becomes possible to apply to a polyethylene terephthalate film.

Patent Document 1 discloses a method of depositing metallic copper by heating a composition containing copper, two formate ions coordinated to the copper, and two $C_9$-$C_{20}$ alkyl imidazoles coordinated to copper through nitrogen. However, the adhesion to a base material and the pattern formation are not mentioned, and the technique for circuit formation is not disclosed. In addition, this composition is aimed at being used in a supercritical fluid such as supercritical carbon dioxide, etc., and its use at atmospheric pressure is not shown and it is not suitable for the formation of a copper film on a hydrophilic surface because of its high hydrophobicity.

Patent Document 2 discloses a method of depositing a copper film by heating a mixed product composed of a copper formate and an alkoxyalkylamine. However, the adhesion to a base material is not disclosed and the formation of a copper film at 130° C. or lower is not described.

Patent Document 3 discloses a method for manufacturing a copper film by heating a copper compound composed of a copper formate and ammonia. However, the formation of a copper film at 130° C. or lower is not described.

Patent Document 4 discloses a method for manufacturing a copper film by heating a copper precursor composition obtained by blending a copper formate and a propanediol compound. However, the formation of a copper film at 130° C. or lower is not described.

In addition, Non-Patent Document 1 describes a purification of a dimeric copper (II) complex with 1-methylimidazole by adding a copper formate to an ethanol solution containing excessive 1-methylimidazole. However, the contents thereof are concerned with a consideration regarding chemical structures, but a description regarding the formation of a copper film is not seen.

PRIOR ART DOCUMENTS

Patent Documents

Patent Document 1: JP-T-2005-513117
Patent Document 2: JP-A-2005-2471
Patent Document 3: JP-A-2005-35984
Patent Document 4: JP-A-2009-256218

Non-Patent Document

Non-Patent Document 1: *Thermochimica Acta*, 98, 139-145 (1986)

SUMMARY OF THE INVENTION

Problem to be Solved by the Invention

The present invention has been made under the above-described conventional actual circumstances, and an object thereof is to provide a copper film-forming agent capable of forming a copper film under an atmospheric pressure at a temperature of 130° C. or lower and also capable of forming a uniform copper film having excellent affinity with a hydrophilic surface and a method for forming a copper film.

Means for Solving the Problem

In order to solve the above-described problem, the present inventors made extensive and intensive investigations. As a result, they found that a desired object can be attained by using a copper film-forming agent containing a copper complex composed of a copper formate and a specified nitrogen-containing heterocyclic compound, leading to accomplishment of the present invention.

That is, the present invention can be accomplished by the following (1) to (20).

(1) A copper film-forming agent containing a copper complex composed of a copper formate and a 5-membered or 6-membered nitrogen-containing heterocyclic compound having from 1 to 3 nitrogen atoms, in which the nitrogen-containing heterocyclic compound has one or two ring structures, the total number of carbon atoms contained in a substituent is from 1 to 5, and an element other than a carbon atom in the compound is not bonded to a hydrogen atom.

(2) The copper film-forming agent according to (1), in which the substituent is selected from the group consisting of an alkyl group, an alkenyl group, an alkynyl group, an alkoxyl group, and an alkoxylalkyl group.

(3) The copper film-forming agent according to (1) or (2), in which the nitrogen-containing heterocyclic compound is an imidazole compound represented by the following formula (I).

[Chem. 1]

(In the formula (I), $R_1$ represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_2$ or $R_4$ to form a heterocyclic ring; and each of $R_2$ to $R_4$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_1$, $R_3$ or $R_4$ to form a ring or a heterocyclic ring, provided that a total of the carbon atoms contained in $R_1$ to $R_4$ is 5 or less).

(4) The copper film-forming agent according to claim (3), in which the imidazole compound represented by the formula (I) is at least one member selected from the group consisting of 1-methylimidazole, 1-ethylimidazole, 1,2-dimethylimidazole, 1-ethyl-2-methylimidazole, 2-ethyl-1-methylimidazole, 1-propylimidazole, 1-isopropylimidazole, 1-butylimidazole, 1-pentylimidazole, 1-vinylimidazole, and 1-allylimidazole.

(5) The copper film-forming agent according to (1) or (2), in which the nitrogen-containing heterocyclic compound is a triazole compound represented by the following formula (IIa) or (IIb).

[Chem. 2]

(In the formulae (IIa) and (IIb), each of $R_5$ and $R_8$ independently represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_7$ or $R_{10}$ to form a heterocyclic ring; each of $R_6$ and $R_7$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_5$, $R_6$ or $R_7$ to form a ring or a heterocyclic ring; $R_9$ represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom; $R_{10}$ represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_8$ to form a heterocyclic ring, provided that all of a total of the carbons contained in $R_5$ to $R_7$ and a total of the carbons contained in $R_8$ to $R_{10}$ are 5 or less).

(6) The copper film-forming agent according to (1) or (2), in which the nitrogen-containing heterocyclic compound is a pyridine compound represented by the following formula (III).

[Chem. 3]

(in the formula (III), each of $R_{11}$ to $R_{15}$ independently represents a hydrogen atom, a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_{11}$, $R_{12}$, $R_{13}$, $R_{14}$ or $R_{15}$ to form a ring or a heterocyclic ring, provided that a total of carbons contained in $R_{11}$ to $R_{15}$ is 5 or less).

(7) The copper film-forming agent according to (1) or (2), in which the nitrogen-containing heterocyclic compound is a pyrazole compound represented by the following formula (IV):

[Chem. 4]

(IV)

(In the formula (IV), $R_{16}$ represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_{19}$ to form a heterocyclic ring; and each of $R_{17}$ to $R_{19}$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_{16}$, $R_{17}$, $R_{18}$ or $R_{19}$ to form a ring or a heterocyclic ring, provided that a total of the carbon atoms contained in $R_{16}$ to $R_{19}$ is 5 or less).

(8) The copper film-forming agent according to any one of (1) to (7), containing an organic solvent or water.
(9) The copper film-forming agent according to any one of (1) to (8), containing a metallic powder.
(10) A method for forming a copper film, containing: a coating step of coating the copper film-forming agent described in any one of (1) to (9) on a base material to form a coating film; and a heating step of heating and burning the coating film at an atmospheric pressure.
(11) The method for forming a copper film according to (10), in which the base material surface is subjected to a hydrophilization treatment prior to the coating step.
(12) The method for forming a copper film according to (10) or (11), in which the heating step is performed at a temperature of 130° C. or lower.
(13) The method for forming a copper film according to any one of (10) to (12), in which the heating step is performed in an inert gas atmosphere.
(14) The method for forming a copper film according to (13), in which the inert gas atmosphere is a nitrogen atmosphere.
(15) The method for forming a copper film according to any one of (10) to (14), in which the base material is at least one member selected from the group consisting of a glass base material, a silicon base material, a metallic base material, a ceramic base material, and a resin base material.
(16) The method for forming a copper film according to any one of (10) to (15), in which the coating step is performed by at least one method selected from the group consisting of a spin coating method, a dipping method, a spray coating method, a mist coating method, a flow coating method, a curtain coating method, a roll coating method, a knife coating method, a blade coating method, an air doctor coating method, a bar coating method, a screen printing method, a gravure printing method, a flexo printing method, an offset printing method, and brush coating.
(17) An article provided with a copper film formed by the method for forming a copper film described in any one of (10) to (16).
(18) A wiring board provided with a copper film formed by the method for forming a copper film described in any one of (10) to (16).
(19) A method for manufacturing a wiring board, containing forming a circuit by a semi-additive process or a full additive process, by using a copper film formed by the method for forming a copper film described in any one of (10) to (16) as a seed layer.
(20) A wiring board manufactured by the manufacturing method described in (19).

EFFECT OF THE INVENTION

In accordance with the copper film-forming agent and the method for forming a copper film according to the present invention, it is possible to form a copper film with high uniformity on a hydrophilic base material surface at an atmospheric pressure in a temperature region of 130° C. or lower. According to this, it becomes possible to widen the applicable scope to materials with low heat resistance, which could not be conventionally realized, in particular, materials of Class B Insulation (maximum allowable temperature: 130° C.) as defined in JIS C4003 in the field of electronic materials, such as polyethylene terephthalate films or the like. Also, it becomes possible to ensure the adhesion of the copper film to the base material by a hydrophilization treatment of the base material surface.

In addition, what it is possible to form a copper film at a low temperature means the fact that a sufficient amount of heat can be ensured at a high temperature. Therefore, as compared with the conventional techniques, shortening of burning time and improvement of electrical conductivity can be expected even under a high-temperature burning condition.

MODES FOR CARRYING OUT THE INVENTION

The present invention is hereunder described in detail.
The copper film-forming agent of the present invention contains a copper complex composed of a copper formate and a 5-membered or 6-membered nitrogen-containing heterocyclic compound which has from 1 to 3 nitrogen atoms and is substituted with a specified substituent (hereinafter also referred to simply as "nitrogen-containing heterocyclic compound of the present invention").

The nitrogen-containing heterocyclic compound of the present invention has a 5-membered or 6-membered heterocyclic skeleton having from 1 to 3 nitrogen atoms. The compound has one or two ring structures, the total number of carbons contained in the substituent is from 1 to 5, and an element other than a carbon atom in the compound is not bonded to a hydrogen atom. The nitrogen-containing heterocyclic compound of the present invention, in which a nitrogen-containing heterocyclic compound is substituted with a specified substituent in this way, can be coordinated to a copper ion due to an unshared electron pair on nitrogen.

There is a conventionally known phenomenon in which when a copper formate is heated in a nitrogen atmosphere, a reduction reaction of a copper ion by a formate ion takes place and copper is deposited. In addition, it is also well known that when an amine is coordinated to a copper formate, the temperature of the reduction reaction is lowered. In this respect, it may be presumed that in general, in view of the fact that the higher the pH of the system, the more advanced the reduction reaction is, the basicity of the amine contributes to lowering of temperature of the reduction reaction.

However, in the case of using a primary amine or a secondary amine, since such an amine is bonded to the deposited copper, a residue is easy to remain and good electrical conductivity is hardly achieved while the reduction reaction is advanced at a relatively low temperature. In addition, in the case of using a tertiary amine, while the issue of residue is solved, since the steric hindrance by substituent is large, the tertiary amine cannot be stably coordinated to copper and a sufficient effect for lowering of temperature is not achieved. In addition, there has been also made an attempt in which a polar substituent such as a hydroxyl group, etc. is introduced into a tertiary amine and stable coordination with copper due to its chelating action is made, however, there is involved such a problem that the volatility is impaired so that high-temperature heating is necessary, the basicity of the tertiary amine is too strong so that the reduction reaction is advanced even at an ordinary temperature, or the like. In addition, there has been made an attempt to lower the temperature of reduction reaction by using a certain kind of a metallic catalyst in combination, but any sufficient effect has not been obtained.

In the case of using the nitrogen-containing heterocyclic compound of the present invention, because of an appropriate basicity and small steric hindrance, the compound is able to be stably coordinated to copper and can form a copper formate complex that is relatively stable at an ordinary temperature. The nitrogen-containing heterocyclic compound of the present invention is able to lower the temperature of reduction reaction of copper with formic acid similar to other amines, but after copper is deposited, the compound can be relatively quickly volatilized without being bonded to copper, thereby enabling copper with less residue and having excellent electrical conductivity to be deposited. In particular, the introduction of a specified substituent into the nitrogen-containing heterocyclic compound imparts an appropriate volatility and makes it possible to go through a fluidized state in a process of copper deposition, and hence, there gives rise to such an effect that a copper film with high uniformity can be obtained. In addition, appropriate polarity is given and thus, it becomes possible to keep affinity with the hydrophilic surface even in a fluidized state, and hence, there gives rise to an effect for making it possible to closely contact with a hydrophilic base material surface well.

The above-described substituent is preferably selected from the group consisting of an alkyl group, an alkenyl group, an alkynyl group, an alkoxyl group, and an alkoxylalkyl group.

Specific examples of the nitrogen-containing heterocyclic compound of the present invention are hereunder described.

<Imidazole Compound>

As the nitrogen-containing heterocyclic compound of the present invention, imidazole compounds represented by the following formula (I) can be mentioned.

[Chem. 5]

(In the formula (I), $R_1$ represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_2$ or $R_4$ to form a heterocyclic ring; and each of $R_2$ to $R_4$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_1$, $R_3$ or $R_4$ to form a ring or a heterocyclic ring, provided that a total of the carbon atoms contained in $R_1$ to $R_4$ is 5 or less.)

Examples of $R_1$ include a methyl group, an ethyl group, a propyl group, an isopropyl group, a butyl group, an isobutyl group, a sec-butyl group, a tert-butyl group, a pentyl group, a vinyl group, and the like.

Specifically, examples of the imidazole compound represented by the formula (I) include:
1-methylimidazole,
1-ethylimidazole,
1-propylimidazole,
1-isopropylimidazole,
1-butylimidazole,
1-isobutylimidazole,
1-sec-butylimidazole,
1-tert-butylimidazole,
1-pentylimidazole,
1-isopentylimidazole,
1-(2-methylbutyl)imidazole,
1-(1-methylbutyl)imidazole,
1-(1-ethylpropyl)imidazole,
1-tert-pentylimidazole,
1,2-dimethylimidazole,
1-ethyl-2-methylimidazole,
2-ethyl-1-methylimidazole,
2-methyl-1-propylimidazole,
2-methyl-1-isopropylimidazole,
1-butyl-2-methylimidazole,
1-isobutyl-2-methylimidazole,
1-sec-butyl-2-methylimidazole,
1-tert-butyl-2-methylimidazole,
1,4-dimethylimidazole,
1,2,4-trimethylimidazole,
1,4,5-trimethylimidazole,
1-vinylimidazole,
1-allylimidazole,
1,2,4,5-tetramethylimidazole,
1-methylbenzimidazole,
imidazo[1,5-a]pyridine, and the like.

Incidentally, in carrying out the present invention, it is also possible to use, in addition to appropriate one kind among the imidazole compounds represented by the formula (I), an imidazole compound of a different kind in combination.

<Triazole Compound>

In addition, as the nitrogen-containing heterocyclic compound of the present invention, triazole compounds represented by the following formula (IIa) or formula (IIb) can be mentioned.

[Chem. 6]

(IIa)

(IIb)

(In the formulae (IIa) and (IIb), each of $R_5$ and $R_8$ independently represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_7$ or $R_{10}$ to form a heterocyclic ring; each of $R_6$ and $R_7$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_5$, $R_6$ or $R_7$ to form a ring or a heterocyclic ring; $R_9$ represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom; $R_{10}$ represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_8$ to form a heterocyclic ring, provided that all of a total of the carbons contained in $R_5$ to $R_7$ and a total of the carbons contained in $R_8$ to $R_{10}$ are 5 or less.)

Examples of $R_5$ and $R_8$ include a methyl group, an ethyl group, a propyl group, an isopropyl group, a butyl group, an isobutyl group, a sec-butyl group, a tert-butyl group, a pentyl group, a vinyl group, and the like.

Specific examples of the triazole compound represented by the formula (IIa) or (IIb) include:
1-methyl-1,2,4-triazole,
1-ethyl-1,2,4-triazole,
1-propyl-1,2,4-triazole,
1-isopropyl-1,2,4-triazole,
1-butyl-1,2,4-triazole,
1-methyl-1,2,3-triazole,
1-ethyl-1,2,3-triazole,
1-propyl-1,2,3-triazole,
1-isopropyl-1,2,3-triazole,
1-butyl-1,2,3-triazole,
1-methylbenzotriazole, and the like.

Incidentally, in carrying out the present invention, it is also possible to use, in addition to appropriate one kind among the triazole compounds represented by the formula (IIa) or formula (IIb), a triazole compound of a different kind in combination.

<Pyridine Compound>

In addition, as the nitrogen-containing heterocyclic compound of the present invention, pyridine compounds represented by the following formula (III) can be mentioned.

[Chem. 7]

(III)

(In the formula (III), each of $R_{11}$ to $R_{15}$ independently represents a hydrogen atom, a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_{11}$, $R_{12}$, $R_{13}$, $R_{14}$ or $R_{15}$ to form a ring or a heterocyclic ring, provided that a total of carbons contained in $R_{11}$ to $R_{15}$ is 5 or less.)

Examples of $R_{11}$ to $R_{15}$ include a methyl group, an ethyl group, a propyl group, an isopropyl group, a butyl group, an isobutyl group, a sec-butyl group, a tert-butyl group, a pentyl group, a vinyl group, a methoxy group, an ethoxy group, and the like.

Specific examples of the pyridine compound represented by the formula (III) include:
pyridine,
4-methylpyridine,
4-ethylpyridine,
4-propylpyridine,
4-butylpyridine,
4-pentylpyridine,
quinoline,
isoquinoline,
4-methoxypyridine, and the like.

Incidentally, in carrying out the present invention, it is also possible to use, in addition to appropriate one kind among the pyridine compounds represented by the formula (III), a pyridine compound of a different kind in combination.

<Pyrazole Compound>

In addition, as the nitrogen-containing heterocyclic compound of the present invention, pyrazole compounds represented by the following formula (IV) can be mentioned.

[Chem. 8]

(IV)

(In the formula (IV), $R_{16}$ represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_{19}$ to form a heterocyclic ring; and each of $R_{17}$ to $R_{19}$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_{16}$, $R_{17}$, $R_{18}$ or $R_{19}$ to form a ring or a heterocyclic ring, provided that a total of the carbon atoms contained in $R_{16}$ to $R_{19}$ is 5 or less.)

Examples of $R_{16}$ include a methyl group, an ethyl group, a propyl group, an isopropyl group, a butyl group, an isobutyl group, a sec-butyl group, a tert-butyl group, a pentyl group, a vinyl group, and the like.

Specific examples of the pyrazole compound represented by the formula (IV) include:
1-methylpyrazole,
1-ethylpyrazole,
1-propylpyrazole,
1-isopropylpyrazole,
1-butylpyrazole,
1-pentylpyrazole, and the like.

Incidentally, in carrying out the present invention, it is also possible to use, in addition to appropriate one kind among the pyrazole compounds represented by the formula (IV), a pyrazole compound of a different kind in combination.

<Others>

In addition, as the nitrogen-containing heterocyclic compound of the present invention, pyridazines, pyrimidines, and pyrazines each having two nitrogen atoms, triazines having three nitrogen atoms, and the like can also be exemplified.

As for the nitrogen-containing heterocyclic compound of the present invention, the above-described compounds may be used solely, or may be used in combination of two or more kinds thereof.

As the copper formate, anhydrous copper (II) formate, copper (II) formate dihydrate, copper (II) formate tetrahydrate, and the like can be suitably used. In addition, one obtained by mixing formic acid with one kind or a combination of two or more kinds of a copper compound such as copper (II) oxide or copper (I) oxide, or basic copper (II) carbonate, copper (II) acetate, copper (II) oxalate, etc., thereby forming a copper formate within the system may also be used.

The copper film-forming agent of the present invention is characterized by containing a copper complex composed of the copper formate and the above-described nitrogen-containing heterocyclic compound of the present invention (hereinafter referred to as "copper complex of the present invention").

The copper film-forming agent of the present invention can be easily prepared by merely mixing the nitrogen-containing heterocyclic compound of the present invention and the copper formate as raw materials, optionally adding a solvent, optionally pulverizing, and kneading, and a special synthesis operation is not required.

The copper complex of the present invention has only to be contained in the copper film-forming agent of the present invention as a composition. The copper complex of the present invention may be separately prepared and then mixed with other components that constitute the copper film-forming agent, or the raw materials that constitute the copper complex of the present invention and other components may be directly mixed to prepare the copper film-forming agent of the present invention.

In the case of separately preparing the copper complex of the present invention, for example, it can be obtained by dissolving or dispersing the copper formate in an appropriate amount of a solvent, adding the nitrogen-containing heterocyclic compound of the present invention thereto, followed by stirring, and then, removing the solvent by means of vacuum distillation.

As the above-described solvent used in preparing the copper complex of the present invention, water, methanol, ethanol, or the like can be preferably used.

As for a proportion of the nitrogen-containing heterocyclic compound of the present invention to the copper formate in the copper film-forming agent of the present invention, the amount of the nitrogen-containing heterocyclic compound of the present invention may be equimolar or more, and is desirably 2 moles or more per mole of the copper formate.

In addition, as for the mixing method of the nitrogen-containing heterocyclic compound of the present invention and the copper formate, besides those as described above, the nitrogen-containing heterocyclic compound of the present invention may be added to a slurry of the copper formate dispersed in a solvent, or the copper formate may be added to a solvent in which the nitrogen-containing heterocyclic compound of the present invention is dissolved.

Examples of the above-described solvent which is used in preparing the copper film-forming agent of the present invention include water, methanol, ethanol, 1-propanol, 2-propanol, 1-butanol, 2-butanol, isobutyl alcohol, tert-butyl alcohol, 1-pentanol, 2-pentanol, 3-pentanol, 1-hexanol, 2-hexanol, 3-hexanol, 1-heptanol, 2-heptanol, 1-octanol, 2-octanol, 2-ethylhexanol, cyclopentanol, cyclohexanol, 2-methoxyethanol, 2-ethoxyethanol, 2-butoxyethanol, ethylene glycol, propylene glycol, propylene glycol monomethyl ether, acetone, ethyl methyl ketone, pentane, hexane, toluene, xylene, tetrahydrofuran, dioxane, methyl formate, ethyl formate, methyl acetate, ethyl acetate, isopropyl acetate, butyl acetate, dimethyl sulfoxide, dimethylformamide, and the like.

The solvent is not particularly limited so long as it is able to form the copper film-forming agent of the present invention in a solution state, a dispersion state, or a paste state, and may be used solely or in combination of two or more kinds thereof. An amount of the solvent may be made a generally adopted amount, and an appropriate ratio may be determined taking into consideration the viscosity and printability of the obtained copper film-forming agent.

The above-described pulverization method has only to be a method capable of making the copper film-forming agent of the present invention into a dispersion state or a paste state in the case of not a solution state, and is not particularly limited.

In the copper film-forming agent of the present invention, in order to increase the thickness of the coating film, a filler such as a particle or powder made of copper, another metal, a resin, a ceramic, or the like, etc. can be used within the range where the effects of the present invention are not impaired.

In addition, in the copper film-forming agent of the present invention, for the purpose of more decreasing the temperature at which a copper film can be formed or shortening the time required for forming a copper film, an alkalizing agent, a metallic catalyst or the like can be used within the range where the effects of the present invention are not impaired. Examples of the alkalizing agent include caustic soda, caustic potash, ammonia, primary amines, secondary amines, tertiary amines, and the like. In addition, examples of the metallic catalyst include silver, platinum, rhodium, palladium, and the like.

In addition, in the copper film-forming agent according to the present invention, additives such as a stabilizer, a dispersant, a viscosity modifier, a surfactant, a pH adjustor, etc. can be used within the range where the effects of the present invention are not impaired.

Next, a method for forming a copper film is described.

The method for forming a copper film of the present invention includes a coating step of coating the copper film-forming agent as described above on a base material to form a coating film; and a heating step of subsequently heating and burning the coating film at an atmospheric pressure.

Examples of the above-described base material include glass base materials, silicon base materials, metallic base materials, ceramic base materials, resin base materials, and the like. Examples of the resin of the resin base material include thermosetting resins such as polyimide resins, epoxy resins, bismaleimide-triazine resins, modified polyphenylene ether resins, etc.; thermoplastic resins such as ABS resins, polyamide resins, polyethylene resins, polypropylene resins, polycarbonate resins, polyethylene terephthalate resins, polyvinyl chloride resins, fluorine resins, liquid crystal polymers, etc.; vegetable fibers such as pulps, celluloses, etc.; and the like.

The above-described base material preferably has a hydrophilic surface, and it is preferable to be subjected to a hydrophilization treatment prior to the coating step as necessary. Examples of the method of the hydrophilization treatment include a dry process such as a plasma treatment, an ultraviolet treatment, an ozone treatment, etc.; a wet process such as an alkali treatment, an acid treatment, etc.; surface modification by graft polymerization or coating film formation; or the like. Conditions of such a hydrophilization treatment cannot be unequivocally specified as it depends upon the material quality or properties of the base material, and the like, and it may be properly set up depending thereon.

Examples of the coating method in the above-described coating step include a spin coating method, a dipping method, a spray coating method, a mist coating method, a flow coating method, a curtain coating method, a roll coating method, a knife coating method, a blade coating method, an air doctor coating method, a bar coating method, a screen printing method, a gravure printing method, an offset printing method, a flexo printing method, brush coating, and the like.

The atmosphere in the above-described heating step is preferably a non-oxidative atmosphere, and examples thereof include a reducing gas, inert gas or deaerated atmosphere, and the like. Examples of the reducing atmosphere include hydrogen, formic acid, and the like, and examples of the inert gas atmosphere include helium, nitrogen, argon, carbon dioxide, and the like. Above all, it is preferable to perform in an inert gas atmosphere from the viewpoints of safety and costs.

Although the heating method is not particularly limited, examples thereof include a method for applying warm air or hot air onto the coated surface; a method for irradiating with a light such as ultraviolet rays, infrared rays, a visible light, etc. for a long time or in a moment; a method for bringing the base material into contact with a heated medium; a method for exposing to a heated gas atmosphere; a method for exposing to a solvent vapor; and the like.

The above-described heating temperature has only to be not lower that the temperature at which the copper complex of the present invention can be decomposed in a treatment atmosphere. A preferred heating temperature cannot be unequivocally specified as it depends upon the kind of the copper complex of the present invention, the kind of the solvent, the atmosphere at the time of heating, and the like, and it may be properly set up depending thereon. Incidentally, when the heating temperature is too high, there is a concern that the base material is deteriorated in the case of a base material having a low heat-resistant temperature, or futility of energy is caused. Thus, the temperature is preferably 150° C. or lower, and more preferably 130° C. or lower. In addition, a lower limit value is preferably not lower than the temperature at which the copper complex of the present invention can be decomposed, and more preferably 100° C. or higher.

Similarly, the heating time cannot be unequivocally specified as it depends upon the kind of the copper complex of the present invention, the kind of the solvent, the atmosphere at the time of heating, and the like, and it may be properly set up depending thereon.

Incidentally, in order to make the film thickness of the copper film thick, coating of the above-described copper film-forming agent and heating can be repeated plural times.

The copper film-forming agent of the present invention can be used for the purpose of coating an arbitrary article in which the formation of a copper film is desired, and the copper film can be formed on a surface of various article by the above-described method for forming a copper film. Examples of this article include wiring boards, films, plates, powders, particles, fibers such as fabrics, nonwoven fabrics, etc., papers, leathers, models, works of art, and the like.

In addition, in manufacturing a wiring board on which a circuit is formed by a semi-additive process or a full additive process, the use of the copper film formed by the above-described method for forming a copper film, as a seed layer, can help to shorten the manufacturing step or to reduce the costs.

EXAMPLES

The present invention is hereunder specifically described by reference to the following Examples and comparative Examples, but it should not be construed that the present invention is limited thereto.

Incidentally, main raw materials as used are as follows.

In addition, raw materials which had not been commercially available were synthesized according to known methods. That is, an imidazole compound in which nitrogen at the 1-position was unsubstituted was treated with sodium hydride in N,N-dimethylformaldehyde and then allowed to react with a corresponding alkyl halide compound under heating, and after a usual post-treatment, the solvent was distilled off under reduced pressure, thereby obtaining a desired product.

[Raw Materials]

Imidazole (manufactured by Wako Pure Chemical Industries, Ltd.)
1-Methylimidazole (ditto)
1-Ethylimidazole (ditto)
1-Butylimidazole (ditto)

1-Propylimidazole (manufactured by Tokyo Chemical Industry Co., Ltd.)
1-Isopropylimidazole (ditto)
1-Vinylimidazole (ditto)
4-Methoxypyridine (ditto)
1-Allylimidazole (manufactured by Alfa Aesar)
1-Methyl-1,2,4-triazole (ditto)
2-Ethyl-1-methylimidazole (synthesized from 2-ethylimidazole (a trade name: 2EZ, manufactured by Shikoku Chemicals Corporation))
1-Ethyl-2-methylimidazole (synthesized from 2-methylimidazole (a trade name: 2MZ, manufactured by Shikoku Chemicals Corporation))
1-Pentylimidazole (synthesized from imidazole (manufactured by Wako Pure Chemical Industries, Ltd.)
1-Hexylimidazole (synthesized from imidazole (manufactured by Wako Pure Chemical Industries, Ltd.)
2-Ethyl-1-hexyl-4-methylimidazole (synthesized from 2-ethyl-4-methylimidazole (a trade name: 2E4MZ, manufactured by Shikoku Chemicals Corporation))
1-Octylimidazole (manufactured by Aldrich)
Pyridazine (ditto)
1,2-Dimethylimidazole (a trade name: 1,2DMZ, manufactured by Shikoku Chemicals Corporation)
1-Benzyl-2-methylimidazole (a trade name: 1B2MZ, manufactured by Shikoku Chemicals Corporation)
2-Methylimidazole (a trade name: 2MZ, manufactured by Shikoku Chemicals Corporation)
4-Methylimidazole (a trade name: 4MZ, manufactured by Shikoku Chemicals Corporation)
3-(Dimethylamino)-1,2-propanediol (manufactured by Wako Pure Chemical Industries, Ltd.)
Copper (II) formate tetrahydrate (ditto)

Test Example 1

Copper complexes used for the preparation of a copper film-forming agent in Examples 1 to 4 and Comparative Examples 1 to 5 are described below, and synthesis examples thereof are described in Reference Examples 1 to 9.
[Copper Complexes]
1-Methylimidazole copper complex (abbreviated as "1MZ-Cu")
1-Ethylimidazole copper complex (abbreviated as "1EZ-Cu")
1-Butylimidazole copper complex (abbreviated as "1BZ-Cu")
1,2-Dimethylimidazole copper complex (abbreviated as "1,2MZ-Cu")
Imidazole copper complex (abbreviated as "SZ-Cu")
2-Methylimidazole copper complex (abbreviated as "2MZ-Cu")
4-Methylimidazole copper complex (abbreviated as "4MZ-Cu")
3-(Dimethylamino)-1,2-propanediol copper complex (abbreviated as "DMA-Cu")
Ammonia copper complex (abbreviated as "NH4-Cu")

Reference Example 1

Synthesis of 1MZ-Cu

In a mortar 2.26 g of copper (II) formate tetrahydrate was finely pulverized and then, dispersed in 100 mL of methanol. Thereto was added 1.64 g of 1-methylimidazole, followed by stirring at a room temperature, to thereby obtain a blue transparent solution. Subsequently, the solvent was distilled off under reduced pressure to obtain 3.0 g of 1-methylimidazole copper complex as a blue solid.

Reference Example 2

Synthesis of 1EZ-Cu

A synthesis operation was performed in accordance with the method of Reference Example 1, except that 1.64 g of the 1-methylimidazole of Reference Example 1 was replaced by 1.92 g of 1-ethylimidazole, thereby obtaining 3.3 g of 1-ethylimidazole copper complex as a blue viscous liquid.

Reference Example 3

Synthesis of 1BZ-Cu

A synthesis operation was performed in accordance with the method of Reference Example 1, except that 1.64 g of the 1-methylimidazole of Reference Example 1 was replaced by 2.48 g of 1-butylimidazole, thereby obtaining 3.8 g of 1-butylimidazole copper complex as a blue liquid.

Reference Example 4

Synthesis of 1,2MZ-Cu

A synthesis operation was performed in accordance with the method of Reference Example 1, except that 1.64 g of the 1-methylimidazole of Reference Example 1 was replaced by 1.92 g of 1,2-dimethylimidazole, thereby obtaining 3.3 g of 1,2-dimethylimidazole copper complex as a blue solid.

Reference Example 5

Synthesis of SZ-Cu

A synthesis operation was performed in accordance with the method of Reference Example 1, except that 1.64 g of the 1-methylimidazole of Reference Example 1 was replaced by 1.36 g of imidazole, thereby obtaining 2.7 g of imidazole copper complex as a blue solid.

Reference Example 6

Synthesis of 2MZ-Cu

A synthesis operation was performed in accordance with the method of Reference Example 1, except that 1.64 g of the 1-methylimidazole of Reference Example 1 was replaced by 1.64 g of 2-methylimidazole, thereby obtaining 3.0 g of 2-methylimidazole copper complex as a blue solid.

Reference Example 7

Synthesis of 4MZ-Cu

A synthesis operation was performed in accordance with the method of Reference Example 1, except that 1.64 g of the 1-methylimidazole of Reference Example 1 was replaced by 1.64 g of 4-methylimidazole, thereby obtaining 3.0 g of 4-methylimidazole copper complex as a blue solid.

Reference Example 8

Synthesis of DMA-Cu

A synthesis operation was performed in accordance with the method of Reference Example 1, except that 1.64 g of the 1-methylimidazole of Reference Example 1 was replaced by 2.38 g of 3-(dimethylamino)-1,2-propanediol, thereby obtaining 3.7 g of 3-(dimethylamino)-1,2-propanediol copper complex as a blue liquid.

Reference Example 9

Synthesis of NH4-Cu

A synthesis operation was performed in accordance with the method of Reference Example 1, except that 1.64 g of the 1-methylimidazole of Reference Example 1 was replaced by 1.36 g of 25% ammonia water, thereby obtaining 1.8 g of ammonia copper complex as a blue solid.

Evaluation test methods adopted in Examples 1 to 4 and Comparative Examples 1 to 5 are as follows.

[Fabrication of Test Piece]

Among the copper complexes, a solid or viscous liquid one was added with diethylene glycol in a proportion shown in Table 1 or 2 and kneaded, pulverized in a mortar as necessary, and formed into a paste state, thereby preparing a copper film-forming agent. A liquid one was used as a copper film-forming agent as it was.

In order to compare the affinity of the copper film-forming agent with a hydrophilic surface, a glass which is originally hydrophilic was used as a base material.

On a slide glass having a size of 48 mm (length)×28 mm (width)×1.2 to 1.5 mm (thickness), the copper film-forming agent was printed in a single pattern having a size of 30 mm (length)×10 mm (width)×0.1 mm (thickness) by using a bar coater. Subsequently, the resultant was put into an oven and heated in a nitrogen atmosphere at the atmospheric pressure at 130° C. for 30 minutes to form a copper film, followed by returning to a room temperature. There was thus fabricated a test piece.

[External Appearance of Copper Film]

The external appearance and aspect of the copper film formed on the test piece was confirmed through visual inspection. The case where the copper film was formed in a copper-colored film-like state was determined as "good external appearance", whereas the case where the copper film was discolored or deposited in a powdered state was determined as "defective external appearance".

AA: Good external appearance (in a copper-colored film-like state)

BB: Defective external appearance (in a brown film-like state or powdered state)

[SEM Photographic Observation of Copper Film]

By using a scanning electron microscope ("S-4800", manufactured by Hitachi, Ltd.), SEM photography was performed at an accelerating voltage of 5 kV at a magnification of 3,000 times and 30,000 times.

[Measurement of Deposition Temperature]

By using TG-DTA ("EXSTAR 6000-TG/DTA 6300", manufactured by Seiko Instruments Inc.), the temperature was raised at a nitrogen flow rate of 500 mL/min from a room temperature to 200° C. at a temperature rise rate of 10° C./min. An exothermic peak temperature after exhibiting heat absorption accompanied by a weight reduction was recorded as a deposition temperature. Incidentally, the deposition temperature is a parameter that is a target for setting up the temperature in heating and burning the copper film-forming agent but does not mean a temperature at which a copper film can be formed.

[Measurement of Resistance Value]

By using a low resistivity meter ("LORESTA GP" with an AP probe, manufactured by Mitsubishi Chemical Analytech Co., Ltd.), a resistance value of the copper film formed on the test piece was measured.

[Adhesion Test]

The copper film formed on the test piece was rubbed by a cotton swab, thereby confirming the adhesion. The case where the copper film did not easily peel off was determined as "good adhesion", whereas the case where the copper film peeled off was determined as "defective adhesion".

AA: Good adhesion

BB: Defective adhesion

Examples 1 to 4

Each of test pieces was fabricated by using a copper film-forming agent having a formulation shown in Table 1, and the resulting copper film was subjected to evaluation of external appearance, measurement of deposition temperature, measurement of resistance value, and adhesion test. The obtained test results are shown in Table 1.

Figure 1:
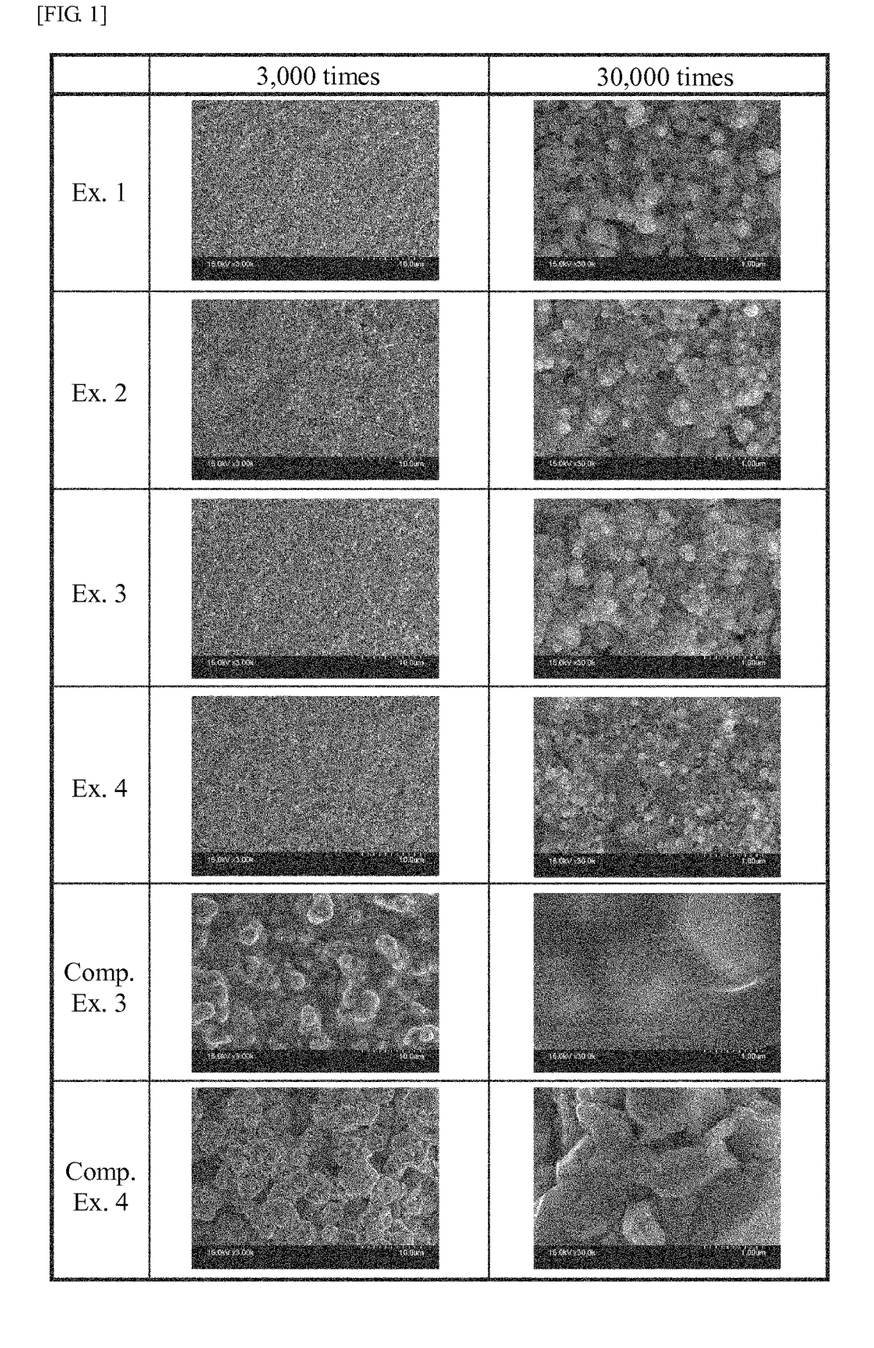
FIG. 1 is an explanatory view showing a SEM photographed image of each of test pieces of Examples 1 to 4 and Comparative Examples 3 and 4.

In addition, SEM photographed images of the test pieces are shown in FIG. 1.

Comparative Examples 1 to 5

Each of test pieces was fabricated by using a copper film-forming agent having a formulation shown in Table 2, and the resulting copper film was subjected to evaluation of external appearance, measurement of deposition temperature, measurement of resistance value, and adhesion test. The obtained test results are shown in Table 2.

In addition, SEM photographed images of the test pieces of Comparative Examples 3 and 4 are shown in FIG. 1.

TABLE 1

|  |  | Example | | | |
|---|---|---|---|---|---|
|  |  | 1 | 2 | 3 | 4 |
| Formulation (wt %) | 1MZ-Cu | 83 |  |  |  |
|  | 1EZ-Cu |  | 95 |  |  |
|  | 1BZ-Cu |  |  | 100 |  |
|  | 1,2MZ-Cu |  |  |  | 83 |
|  | Diethylene glycol | 17 | 5 |  | 17 |
| Evaluation test | External appearance | AA | AA | AA | AA |
|  | Deposition temperature (° C.) | 131.2 | 118.3 | 114.9 | 124.0 |
|  | Resistance value (Ω) | $3.8 \times 10^{-2}$ | $8.1 \times 10^{-2}$ | $6.1 \times 10^{-2}$ | $2.9 \times 10^{0}$ |
|  | Adhesion | AA | AA | AA | AA |

TABLE 2

| | | Comparative Example | | | | |
|---|---|---|---|---|---|---|
| | | 1 | 2 | 3 | 4 | 5 |
| Formu-lation (wt %) | SZ-Cu | 83 | | | | |
| | 2MZ-Cu | | 83 | | | |
| | 4MZ-Cu | | | 83 | | |
| | DMA-Cu | | | | 100 | |
| | NH4—Cu | | | | | 28 |
| | Diethylene glycol | 17 | 17 | 17 | | 72 |
| Evalu-ation test | External appearance | BB (Brown film-like state) | BB (Brown film-like state) | BB (Brown film-like state) | BB (Pow-dered state) | BB (Pow-dered state) |
| | Deposition temperature (° C.) | 149.4 | 150.4 | 166.4 | 136.4 | 160.6 |
| | Resistance value (Ω) | >$10^7$ | >$10^7$ | >$10^7$ | >$10^7$ | $1.7 \times 10^{-1}$ |
| | Adhesion | BB | BB | BB | BB | BB |

According to the test results shown in Table 1, Table 2 and FIG. 1, the use of the copper film-forming agent of the present invention can form a copper film with high uniformity on a hydrophilic surface of a base material at an atmospheric pressure in a temperature region of 130° C. or lower.

In addition, from the results of FIG. 1, dense copper films with high uniformity were formed in the test pieces of Examples 1 to 4; whereas an organic material residue was present in the copper surface in the test piece of Comparative Example 3 and coarse copper particles were deposited in the test piece of Comparative Example 4, and both did not provide a uniform copper film.

Test Example 2

Test pieces of Examples 5 to 21 and Comparative Examples 6 to 11 were fabricated by the following method and then subjected to the following tests.

[Fabrication of Test Piece]

A nitrogen-containing heterocyclic compound and copper formate tetrahydrate were compounded in a proportion shown in Table 3 or 4 and kneaded. A solid or viscous liquid one was added with diethylene glycol and kneaded, pulverized in a mortar as necessary, and formed in a paste, thereby preparing a copper film-forming agent. A liquid one even without being added with ethylene glycol was used as a copper film-forming agent as it was.

In order to compare the affinity of the copper film-forming agent with the hydrophilic surface, a glass which is originally hydrophilic was used as a base material.

On a slide glass having a size of 48 mm (length)×28 min (width)×1.2 to 1.5 mm (thickness), polyimide tapes having a thickness of 0.055 mm were laminated in parallel at intervals of 10 mm, the copper film-forming agent was built up on the intervals, and the surplus was scraped off with a plate, thereby printing the copper film-forming agent in a single pattern having a size of 30 mm (length)×10 mm (width)×0.055 mm (thickness). Subsequently, the resultant was heated by using a hot plate in a nitrogen atmosphere at 130° C. for 30 minutes to form a copper film, followed by returning to a room temperature. There was thus fabricated a test piece.

[External Appearance of Copper Film]

The external appearance and aspect of the copper film formed on the test piece was confirmed through visual inspection. The case where the copper film was formed in a copper-colored film-like state was determined as "good external appearance", whereas the case where the copper film was uneven or was not solidified was determined as "defective external appearance".

AA: Good external appearance (in a copper-colored film-like state)

BB: Defective external appearance (uneven or not solidified (wet), or in a black film-like state)

[CCD Photographic Observation of Copper Film]

By using a microscopic CCD camera ("DS-5M-U1", manufactured Nikon Corporation), CCD photography was performed at a magnification of 7 times.

[Measurement of Resistance Value]

By using a low resistivity meter ("LORESTA GP" with a TFP probe, manufactured by Mitsubishi Chemical Analytech Co., Ltd.), a resistance value of the copper film formed on the test piece was measured. However, with respect to a test piece which did not become in a uniform film-like state, the measurement thereof was not performed upon determination that it may not function originally as a conductor.

[Adhesion Test]

The copper film formed on the test piece was rubbed by a cotton swab, thereby confirming the adhesion. The case where the copper film did not easily peel off was determined as "good adhesion", whereas the case where the copper film peeled off was determined as "defective adhesion".

AA: Good adhesion
BB: Defective adhesion

Examples 5 to 21

Each of test pieces was fabricated by using a copper film-forming agent having a formulation shown in Table 3, and the resulting copper film was subjected to evaluation of external appearance, measurement of resistance value, and adhesion test. The obtained test results are shown in Table 3.

Figure 2:
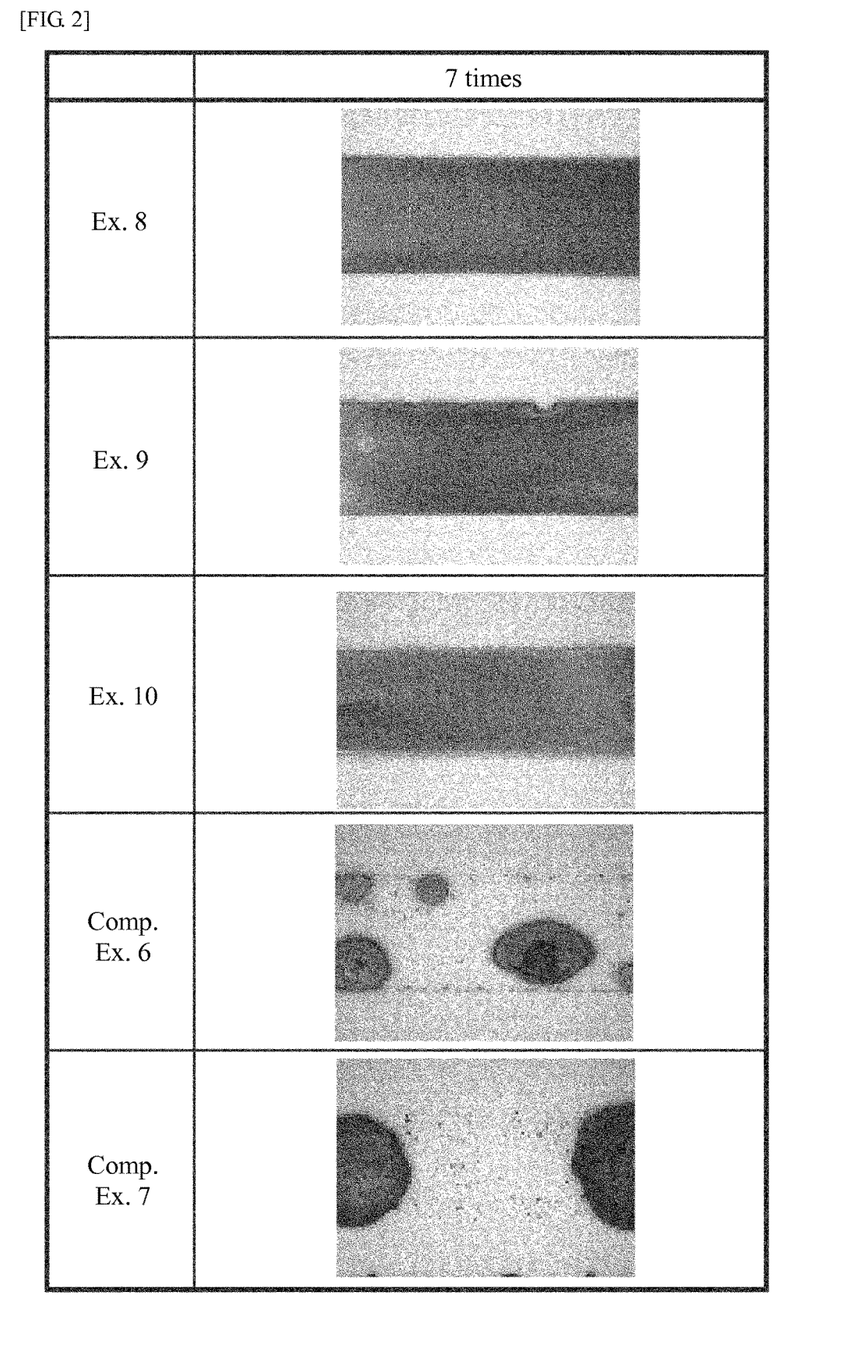
FIG. 2 is an explanatory view showing a CCD photographed image of each of test pieces of Examples 8 to 10 and Comparative Examples 6 and 7.

In addition, CCD photographed images of the test pieces of Examples 8 to 10 are shown in FIG. 2.

Comparative Examples 6 to 11

Each of test pieces was fabricated by using a copper film-forming agent having a formulation shown in Table 4, and the resulting copper film was subjected to evaluation of external appearance, measurement of resistance value, and adhesion test. The obtained test results are shown in Table 4.

In addition, CCD photographed images of the test pieces of Comparative Examples 6 and 7 are shown in FIG. 2.

TABLE 3

| | | Example | | | | | | | | | | | | | | | |
|---|---|---|---|---|---|---|---|---|---|---|---|---|---|---|---|---|---|
| | | 5 | 6 | 7 | 8 | 9 | 16 | 10 | 11 | 12 | 13 | 14 | 15 | 17 | 18 | 19 | 20 | 21 |
| Copper formate tetrahydrate | | | 2.26 | 2.26 | 2.26 | 2.26 | 2.26 | 2.26 | 2.26 | 2.26 | 2.26 | 2.26 | 2.26 | 2.26 | 2.26 | 2.26 | 2.26 | 2.26 |

TABLE 3-continued

| | | Example | | | | | | | | | | | | | | | | |
|---|---|---|---|---|---|---|---|---|---|---|---|---|---|---|---|---|---|---|
| | | 5 | 6 | 7 | 8 | 9 | 16 | 10 | 11 | 12 | 13 | 14 | 15 | 17 | 18 | 19 | 20 | 21 |
| Formulation (wt %) | 1MZ-Cu | 3.17 | | | | | | | | | | | | | | | | |
| | 1-Methyimidazole | | 3.28 | 1.23 | 1.64 | | | | | | | | | | | | | |
| | 1-Ethylimidazole | | | | | 1.96 | | | | | | | | | | | | |
| | 1-Butylimidazole | | | | | | 2.48 | | | | | | | | | | | |
| | 1-Propylimidazole | | | | | | | | 2.20 | | | | | | | | | |
| | 1-Isopropylimidazole | | | | | | | | | 2.20 | | | | | | | | |
| | 1-Vinylimidazole | | | | | | | | | | 1.88 | | | | | | | |
| | 1-Methyl-2-ethylimidazole | | | | | | | | | | | 2.20 | | | | | | |
| | 1-Ethyl-2-methylimidazole | | | | | | | | | | | | 2.20 | | | | | |
| | 1-Allylimidazole | | | | | | | | | | | | | 2.16 | | | | |
| | 1-Pentylimidazole | | | | | | | | | | | | | | 2.76 | | | |
| | Quinoline | | | | | | | | | | | | | | | 2.58 | | |
| | 4-Methoxypyridine | | | | | | | | | | | | | | | | 2.18 | |
| | Pyridazine | | | | | | | | | | | | | | | | | 1.60 | |
| | 1-Methyl-1,2,4-triazole | | | | | | | | | | | | | | | | | | 1.66 |
| | Ethylene glycol | 0.62 | | 0.62 | 0.62 | | | | | | 1.24 | 1.24 | | | | 2.48 | 1.24 | 0.62 | 2.48 |
| Evaluation test | External appearance | AA | AA | AA | AA | AA | AA | AA | AA | AA | AA | AA | AA | AA | AA | AA | AA | AA |
| | Resistance value (Ω) | 0.02 | 0.02 | 0.02 | 0.02 | 0.04 | 0.08 | 0.04 | 0.04 | 0.03 | 0.03 | 0.04 | 0.04 | 0.02 | 0.47 | 0.01 | 1.44 | 0.09 |
| | Adhesion | AA | AA | AA | AA | AA | AA | AA | AA | AA | AA | AA | AA | AA | AA | AA | AA | AA |

TABLE 4

| | | Comparative Example | | | | | |
|---|---|---|---|---|---|---|---|
| | | 6 | 7 | 8 | 9 | 10 | 11 |
| Formulation (wt %) | Copper formate tetrahydrate | 2.26 | 2.26 | 2.26 | 2.26 | 2.26 | 2.26 |
| | 1-Hexylimidazole | 3.05 | | | | | |
| | 1-Octylimidazole | | 3.61 | | | | |
| | 1-Hexyl-2-ethyl-4-methylimidazole | | | 3.89 | | | |
| | 1-Methyl-2-undecylimidazole | | | | 4.73 | | |
| | 1-Benzyl-2-methylimidazole | | | | | 3.45 | |
| | 1-Methyl-1H-tetrazole | | | | | | 1.68 |
| | Ethylene glycol | | 1.24 | 1.24 | 2.48 | 0.62 | 0.62 |
| Evaluation test | External appearance | BB (Uneven) | BB (Uneven) | BB (Uneven) | BB (Uneven) | BB (Wet) | BB (Black film-like state) |
| | Resistance value (Ω) | — | — | — | — | >10$^7$ | >10$^7$ |
| | Adhesion | AA | AA | AA | BB | BB | AA |

According to the test results shown in Table 3, Table 4 and FIG. 2, the use of the copper film-forming agent of the present invention can form a copper film with high uniformity on a hydrophilic surface of a base material at an atmospheric pressure in a temperature region of 130° C. or lower. Incidentally, with respect to each of the test pieces of Comparative Examples 6 to 9, a uniform coating film was not formed, and therefore, the measurement of the resistance value was not performed upon determination that it may not function as a conductor.

In addition, from the results of FIG. 2, a uniform film was formed in the test pieces of Examples 8 to 10 without causing repellence on the glass surface; whereas in the test pieces of Comparative Examples 6 and 7, repellence on the glass surface was caused, so that a uniform film was not formed.

Test Example 3

The copper film-forming agents of the present invention were subjected to confirmation tests regarding the formation and processing of a copper film relative to base materials having various material qualities or properties by the following methods.

Example 22

In 40 g of methanol was dissolved 26 g of 1-methylimidazole, thereto was then added 36 g of copper formate tetrahydrate, followed by stirring and dissolving, to thereby prepare a methanol solution of 1MZ-Cu. There was thus prepared a copper film-forming agent. A pulp paper ("KIM-WIPES S-200", manufactured by Nippon Paper Crecia Co., Ltd.) which had been cut in a size of 30 mm square was dipped therein and then lifted up, followed by drying in air. This was hung in an oven and heated in a nitrogen atmosphere at 130° C. for 30 minutes to form a copper film, followed by returning to a room temperature and taking out. The taken out paper presented a copper color. Its electrical conductivity was confirmed by using a low resistivity meter ("LORESTA GP" with a TFP probe, manufactured by Mitsubishi Chemical Analytech Co., Ltd.). As a result, it showed a resistance value of 6.14Ω.

Example 23

To the copper film-forming agent prepared in Example 22 was added 2 g of zeolite ("Boiling Stone", manufactured by Wako Pure Chemical Industries, Ltd.), followed by stirring at an ordinary temperature for one minute. This was collected by filtration, transferred onto an evaporating dish, naturally dried, then put into an oven, and heated in a nitrogen atmosphere at 130° C. for 30 minutes, followed by returning to a room temperature and taking out. The taken out zeolite presented a brown color, and one grain thereof was sandwiched by a tester and confirmed with respect to the electrical conductivity. As a result, it showed a resistance value of 50Ω.

Example 24

A polyethylene terephthalate film ("LUMIRROR S10", manufacture by Toray Industries, Inc.) having a thickness of 0.125 mm, which had been cut in a size of 50 mm (length)× 30 mm (width), was prepared and subjected to a hydrophilization treatment upon irradiation with a UV light of 172 nm for 5 minutes by using a UV irradiator ("MIN-EXCIMER", manufactured by Ushio Inc.). By using the copper film-forming agent prepared in Example 8, a single pattern having a size of 30 mm (length)×20 mm (width)×0.055 mm (thickness) was printed on this polyethylene terephthalate film in the same manner as in Example 8. This was heated on a hot plate in a nitrogen atmosphere at 120° C. for 30 minutes to form a copper film, followed by returning to a room temperature and taking out. The taken out sample presented a copper-colored film-like state. It was evaluated with respect to adhesion in accordance with JIS K5400. As a result, the sample exhibited good adhesion without causing peeling of any piece. Its electrical conductivity was confirmed by using a low resistivity meter ("LORESTA GP" with a TFP probe, manufactured by Mitsubishi Chemical Analytech Co., Ltd.). As a result, it showed a resistance value of 0.03Ω.

Example 25

Electrolytic copper plating was applied on the copper film fabricated in Example 24 by using a commercially available copper sulfate plating bath. As a result, a copper-plated coating film was formed without causing any problem.

While the present invention has been described in detail and with reference to specific embodiments thereof, it will be apparent to one skilled in the art that various changes and modifications can be made therein without departing from the spirit and scope thereof. The present application is based on Japanese patent application (No. 2012-154124) filed on Jul. 9, 2012, the entirety of which is incorporated herein by reference.

INDUSTRIAL APPLICABILITY

The copper film-forming agent and the method for forming a copper film according to the present invention are useful as materials and means for forming conductors such as wirings, electrodes, etc. in various fields. For example, they can be used for, in addition to printed wiring boards, RF-ID tags, NFC antennas, flat displays, solar cells, laminated ceramic capacitors, chip resistors, planar coils, printed transistors by printed electronics, and the like. In addition, they are expected to apply to wide fields, for example, metal support on a porous catalyst, electrification prevention of fibers or leathers, electromagnetic shielding processing, decorating materials, and the like.

The invention claimed is:
1. A method for forming a copper film, comprising: a coating step of coating on a base material to form a coating film a copper film-forming agent comprising a copper complex composed of a copper formate and an imidazole compound represented by the following formula (I):

[Chem. 1]

in the formula (I), $R_1$ represents a linear, branched or cyclic hydrocarbon group having from 1 to 5 carbon atoms, or a linear, branched or cyclic substituent containing a hydrocarbon having from 1 to 5 carbon atoms and an element other than a carbon atom, the element being not bonded to a hydrogen atom, or is bonded to adjacent $R_2$ or $R_4$ to form a heterocyclic ring; and each of $R_2$ to $R_4$ independently represents a hydrogen atom, a linear, branched or cyclic hydrocarbon group having from 1 to 4 carbon atoms, or a linear, branched or cyclic substituent containing a hydrocarbon having from 1 to 4 carbon atoms and an element other than a carbon atom, the element being not bonded to a hydrogen atom, or is bonded to adjacent $R_1$, $R_3$ or $R_4$ to form a ring or a heterocyclic ring, provided that a total of the carbon atoms contained in $R_1$ to $R_4$ is 5 or less; and
a heating step of heating and burning the coating film at an atmospheric pressure.
2. The method for forming a copper film according to claim 1, wherein the base material surface is subjected to a hydrophilization treatment prior to the coating step.
3. The method for forming a copper film according to claim 1, wherein the heating step is performed at a temperature of 130° C. or lower.
4. The method for forming a copper film according to claim 1, wherein the heating step is performed in an inert gas atmosphere.
5. The method for forming a copper film according to claim 4, wherein the inert gas atmosphere is a nitrogen atmosphere.
6. The method for forming a copper film according to claim 1, wherein the base material is at least one member selected from the group consisting of a glass base material, a silicon base material, a metallic base material, a ceramic base material, and a resin base material.
7. The method for forming a copper film according to claim 1, wherein the coating step is performed by at least one method selected from the group consisting of a spin coating method, a dipping method, a spray coating method, a mist coating method, a flow coating method, a curtain coating method, a roll coating method, a knife coating method, a blade coating method, an air doctor coating method, a bar coating method, a screen printing method, a gravure printing method, an offset printing method, a flexo printing method, and brush coating.

8. A method for manufacturing a wiring board, comprising forming a circuit by a semi-additive process or a full additive process, by using a copper film formed by the method for forming a copper film described in claim 1 as a seed layer.

* * * * *